United States Patent [19]

Furukawa et al.

[11] Patent Number: 4,582,847

[45] Date of Patent: Apr. 15, 1986

[54] 4-CHLORO-2-PHENYLIMIDAZOLE-5-ACETIC ACID DERIVATIVES AND USE AS DIURETICS AND HYPOTENSIVES

[75] Inventors: Yoshiyasu Furukawa, Takarazuka; Kohei Nishikawa, Kyoto, both of Japan

[73] Assignee: Takeda Chemical Industries, Ltd., Osaka, Japan

[21] Appl. No.: 504,049

[22] PCT Filed: Mar. 14, 1983

[86] PCT No.: PCT/JP83/00078

§ 371 Date: May 17, 1983

§ 102(e) Date: May 17, 1983

[87] PCT Pub. No.: WO83/03250

PCT Pub. Date: Sep. 29, 1983

[51] Int. Cl.$^4$ .................. C07D 233/66; A61K 31/415
[52] U.S. Cl. ........................... 514/400; 548/337
[58] Field of Search ..................... 548/337; 514/400

[56] References Cited

U.S. PATENT DOCUMENTS 4,207,324  6/1980  Matsumura et al. ............... 548/337

FOREIGN PATENT DOCUMENTS 0028834  5/1981  European Pat. Off. ............ 548/337
0028833  5/1981  European Pat. Off. ............ 548/337
  14788 11/1979  Japan ........................... 548/337
1535566 12/1978  United Kingdom ................ 548/337

OTHER PUBLICATIONS

H. Karppanen et al., Agents and Actions, 9, 84–85 (1979).

M. H. Maxwell, Advances in Nephrology, 8, 297–319 (1979).

Primary Examiner—Henry R. Jiles
Assistant Examiner—Robert C. Whittenbaugh
Attorney, Agent, or Firm—Wegner & Bretschneider

[57] ABSTRACT

Compounds of the formula

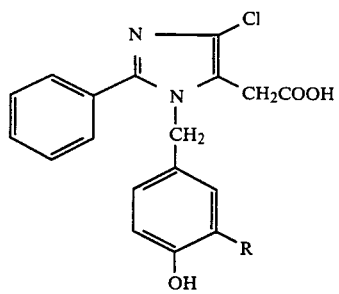

wherein R is lower alkyl, and salts thereof. These compounds have excellent diuretic and antihypertensive actions in mammalian animals and are of use as therapeutic drugs for the treatment of edema and hypertension.

14 Claims, No Drawings

4-CHLORO-2-PHENYLIMIDAZOLE-5-ACETIC ACID DERIVATIVES AND USE AS DIURETICS AND HYPOTENSIVES

DESCRIPTION

1. Technical Field

This invention relates to novel imidazole derivatives having excellent pharmacological actions.

2. Background Art

There are known various imidazole derivatives having diuretic and antihypertensive actions but none of the derivatives so far reported have been clinically satisfactory.

The extensive research undertaken by the present inventors resulted in the successful preparation of imidazole derivatives possessing desirable diuretic and antihypertensive actions and, consequently, in the development of this invenion.

DISCLOSURE OF THE INVENTION

This invention relates to novel imidazole derivatives having excellent pharmacological actions. More particularly, this invention provides compounds of the formula

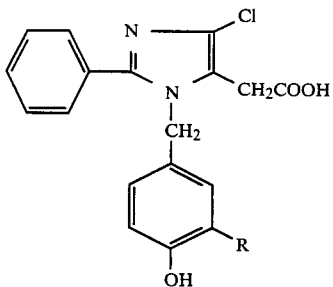

(I)

wherein R is lower alkyl and salts thereof, which have angiotensin II-antagonizing, diuretic and antihypertensive activities and are of use as diuretics and antihypertensives.

Referring to the formula (I), lower alkyl R is preferably of 1 to 3 carbon atoms, such as methyl, ethyl, propyl, i-propyl, etc.

The above-mentioned compound (I) can be produced for example by (A) deprotecting a compound of the formula

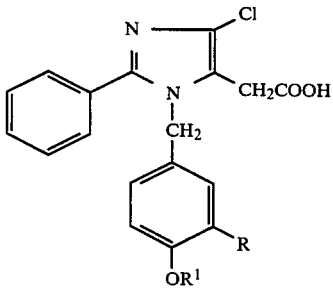

(II)

wherein R is lower alkyl and $R^1$ is a protective group, or, alternatively, by (B) hydrolyzing a compound of the formula

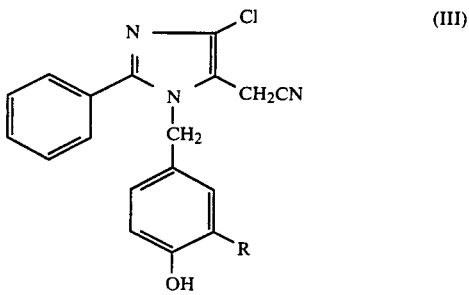

(III)

wherein R is as defined above.

Referring to the above formula (II), the protective group $R^1$ may for example be lower ($C_{1-3}$) alkyl or a benzyl group which may be substituted (by 1 to 3 $C_{1-3}$ alkyl, $C_{1-3}$ alkoxy or/and other groups). The method of deprotection is optional only if it is capable of replacing $R^1$ with a hydrogen atom, e.g. solvolysis, hydrogenolysis or a suitable dealkylation reaction.

When $R^1$ is lower alkyl, there may be mentioned such procedures as 1) heating in the presence of an aqueous hydrogen halide, 2) reaction with trimethylsilyl iodide and subsequent treatment with water, 3) reaction with boron tribromide and subsequent treatment with water and 4) reaction in the copresence of a Lewis acid and a sulfur-containing compound followed by treatment with water, for instance.

In process 1), 1 to 10 hours of heating in 20 to 60% hydrobromic acid at 50° to 150° C. is desirable. In process 2), II is preferably reacted with 1 to 5 equivalents of trimethylsilyl iodide in a solvent such as acetonitrile at 50° to 90° C. for 10 to 50 hours and, then, water is added. In process 3), II is reacted with 1 to 2 equivalents of boron tribromide in a solvent such as dichloromethane at 10° to 30° C. for 1 to 10 hours, followed by treatment with water. In process 4), II is preferably reacted with 3 to 5 equivalents of a Lewis acid and 3 to 30 equivalents of a sulfur-containing compound in a solvent such as dichloromethane at 0° to 30° C. for 1 to 20 hours, followed by treatment with water. The Lewis acid mentioned above is preferably aluminum chloride, ferric chloride or the like, and the sulfur-containing compound is preferably 1,3-ethanedithiol, thiophenol, thioglycolic acid, dimethyl disulfide, diethyl disulfide or the like.

When $R^1$ is said benzyl group which may be substituted; there may be employed the process comprising heating (II) in trifluoroacetic acid for 10 minutes to 1 hour or the catalytic reduction reaction in hydrogen gas streams in the presence of a suitable catalyst such as palladium, Raney nickel or the like.

The hydrolysis of said compound (III) is conducted advantageously in the presence of an alkali or an acid. The alkali is preferably a metal hydroxide such as sodium hydroxide, potassium hydroxide, etc., while the acid is preferably a mineral acid such as hydrochloric acid, sulfuric acid, hydrobromic acid, etc. The solvent is preferably aqueous alcohol. Generally, this reaction is preferably conducted at 50° to 100° C. for 2 to 10 hours.

The resulting compound (I) can be easily isolated by the conventional separation procedure such as aqueous dilution, extraction, neutralization, recrystallization, etc.

The compound (I) can also be obtained by administering a compound of the formula

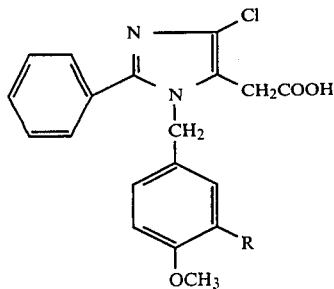

(IV)

wherein R is as defined hereinbefore to a rat and recovering the compound (I) as a metabolite thereof.

The compound (I) can be obtained as salts with a physiologically acceptable acid or base by utilizing the per se conventional procedure. Such salts include acid addition salts e.g. salts with inorganic acids (hydrochloric acid, hydrobromic acid, sulfuric acid, etc.), salts with organic acids (acetic acid, propionic acid, maleic acid, succinic acid, malic acid, etc.) depending on substituents, and salts with bases such as ammonium salts and salts with alkali metals or alkaline earth metals (e.g. sodium, potassium, calcium, etc.), etc.

The compound (I) and salts thereof, which can thus be produced, are of low toxicity, have desirable diuretic actions, and antagonize the vasoconstrictive and hypertensive actions of angiotensin II. Thus, these compounds display excellent diuretic and antihypertensive effects in animals and particularly in mammalian animals (e.g. dog, rabbit, rat, man) and are therefore useful as drugs for the treatment of edema and hypertension due to various causes. When the compound (I) and a salt thereof is used as a drug, it can be administered orally or otherwise, either as it is or as formulated with an appropriate pharmaceutically acceptable carrier, excipient or diluent in such dosage forms as powders, granules, tablets, capsules, injections, etc. The dosage depends on the disease to be treated, the condition and background of the patient or recipient, administration route, etc. For the treatment of essential hypertension in an adult human, for instance, the preferred oral dosage is 10 to 100 mg daily and the preferred intravenous dosage is 5 to 50 mg daily, given in 2 to 3 divided doses.

Of the starting compounds used in the practice of this invention, the compound (III) is a novel compound and can be produced for example by deprotecting a compound of the formula

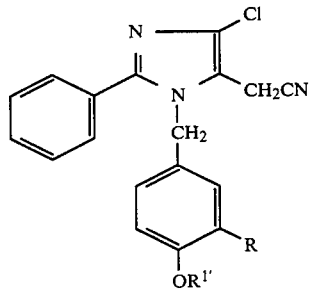

(V)

wherein R is as defined hereinbefore and $R^{1'}$ is a benzyl group which may be substituted. The deprotecting reaction referred to above can be conducted in the same manner as described hereinbefore.

The compound (I) can be produced by treating a compound of the formula

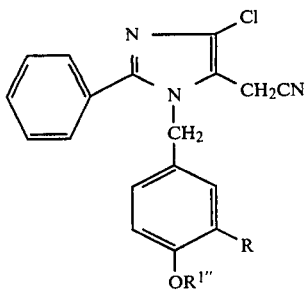

(V')

wherein R is as defined hereinbefore and $R^{1''}$ is lower alkyl, with an acid, in which case both the deprotection and the hydrolysis are accomplished in one operation. In regard of the acid mentioned just above, the one mentioned in 1) of the conditions of deprotection reaction mentioned hereinbefore can be employed with advantage.

In using the compound (I) of this invention as a diuretic or antihypertensive drug, it can be used in the form of a "masked compound", for example as a compound of the formula

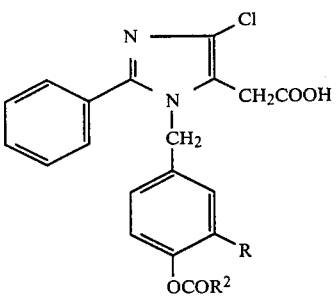

(VI)

wherein R is as defined hereinbefore and $R^2$ is lower alkyl, or a salt thereof.

Referring to the above formula, lower alkyl $R^2$ is preferably a group containing up to 5 carbon atoms, such as methyl, ethyl, propyl, i-propyl, butyl, i-butyl, sec-butyl, t-butyl, etc.

The compound (VI) can be produced for example by acylating the compound (I). Thus, the compound (VI) can be easily produced by reacting the compound (I) with a carboxylic acid of the formula $R^2COOH$ (VII)

wherein $R^2$ is as defined above, or a reactive derivative thereof (e.g. acid halides, acid anhydrides, etc.).

This reaction is carried out in the presence or absence of a solvent. The solvent that can be used includes the common neutral organic solvents such as benzene, chloroform, diethyl ether, etc., basic solvents such as pyridine, picoline, lutidine, etc., and water. If necessary, a dehydrating agent (DCC, p-toluenesulfonic acid, etc.), an inorganic base (NaOH, KOH, $K_2CO_3$, etc.), or an organic base (pyridine, collidine, etc.) may be added.

The reaction proceeds satisfactorily at room temperature, although the reaction may be conducted at elevated temperature (40° to 100° C.) or under cooling (−10° to +10° C.). With respect to the compound (I),

Example 8

4-Chloro-1-(4-methoxy-3-methylbenzyl)-2-phenylimidazole-5-acetic acid (15 g) was added to 270 ml of a dichloromethane solution containing 16.2 g of aluminum chloride and 10 g of 1,3-ethanedithiol and the mixture was stirred at room temperature, whereupon the starting material dissolved once and then a precipitate separated out. The mixture was allowed to stand at room temperature for 6 hours. The supernatant was then discarded, and 50 ml of acetone and 20 ml of water were added to the precipitate. To the resulting solution was added 20 ml of 1N-hydrochloric acid to give a precipitate, which was dissolved in 150 ml of 75% ethanol. The solution was passed through a column of 50 ml of Amberlite IRC-50 (trademark) (H-form) and the column was washed with 75% ethanol. The effluent and washings were combined and diluted with water to the ethanol concentration of 50%. The above procedure gave 12 g of 4-chloro-1-(4-hydroxy-3-methylbenzyl)-2-phenylimidazole-5-acetic acid as colorless scales, m.p. 190°-192° C. (decompn.).

Example 9

Aluminum chloride (1.2 g) and 0.8 ml of dimethyl disulfide were dissolved in 20 ml of dichloromethane, then 1.1 g of 4-chloro-1-(4-methoxy-3-methylbenzyl)-2-phenylimidazole-5-acetic acid was added, and the mixture was stirred at room temperature. During this procedure, the material dissolved once and then a precipitate separated out. After the mixture was allowed to stand at room temperature for 3 hours, the supernatant was discarded and the precipitate was further treated in accordance with the procedure of Example 8 to give 0.8 g of 4-chloro-1-(4-hydroxy-3-methylbenzyl)-2-phenylimidazole-5-acetic acid as colorless scales, m.p. 190°-192° C. (decompn.).

Referring Example 1 o-Cresol (50 g), 70 g of benzyl chloride and 38.5 g of potassium hydroxide were boiled in a mixture of 100 ml of water and 500 ml of ethanol for 4 hours. The solvent was then distilled off and the residue was shaken with 500 ml each of water and diethyl ether. The diethyl ether layer was washed with 10% sodium hydroxide and water in that order, and distilled under reduced pressure to give 70 g of an O-benzylcresol fraction boiling at 130°-133° C./5 mmHg.

The above product (50 g) and 30.5 g of paraformaldehyde were stirred together in 130 ml of concentrated hydrochloric acid at room temperature for 48 hours. The reaction mixture was extracted with two 300-ml portions of hexane and the hexane layer was washed with 10% aqueous sodium hydrogen carbonate and water in that order and evaporated to dryness under reduced pressure to give 59 g of crude 4-benzyloxy-3-methylbenzyl chloride as a colorless oil.

The above product (without purification) was mixed with 31 g of 4-chloro-5-formyl-2-phenylimidazole, and 20 g of potassium carbonate was added. The whole mixture was stirred in 230 ml of dimethylformamide at 100° C. for 5 hours. The reaction mixture was poured into 2 liters of water and extracted with two 500-ml portions of chloroform. The chloroform layer was washed with water and evaporated to dryness under reduced pressure, and the residue was chromatographed on a column of silica gel (700 g) using chloroform as an eluent. The desired fractions were combined and evaporated to dryness under reduced pressure. The residue was dissolved in methanol and the solution was allowed to cool to give 37.5 g of 1-(4-benzyloxy-3-methylbenzyl)-4-chloro-5-formyl-2-phenylimidazole as colorless prisms, m.p. 135°-136° C.

The above product (37 g) was suspended in 300 ml of ethanol, then 3 g of sodium borohydride was added, and the mixture was stirred at 50°-60° C. for 6 hours, at the end of which time it was evaporated to dryness under reduced pressure. The residue was washed with methanol to give 36.5 g of 1-(4-benzyloxy-3-methylbenzyl)-4-chloro-5-hydroxymethyl-2-phenylimidazole as light-yellow prisms, m.p. 184°-186° C.

The above product (36.5 g) was suspended in 200 ml of chloroform, then 14 ml of thionyl chloride was added dropwise, and the mixture was allowed to stand at room temperature for an hour and then evaporated to dryness under reduced pressure. The residue was dissolved in 300 ml of chloroform and the solution was ice-cooled. Sodium cyanide (20 g) and 3 g of tetrabutylammonium bromide were dissolved in 150 ml of ice water and the solution was stirred vigorously with the above-prepared chloroform solution under ice-cooling for 2 hours and at room temperature for 15 hours. The aqueous layer was extracted with chloroform, and the chloroform layers were combined, washed with water and evaporated to dryness under reduced pressure. The residue was chromatographed on a column of silica gel (500 g) using chloroform as an eluent. The desired fractions were combined and evaporated to dryness under reduced pressure. The residue was dissolved in methanol and the solution was allowed to cool to give 35 g of 1-(4-benzyloxy-3-methylbenzyl)-4-chloro-5-cyanomethylimidazole as light-yellow needles, m.p. 102°-105° C.

The above product (30 g) was dissolved in 200 ml of ethanol, 200 ml of 2N-sodium hydroxide was added and the mixture was boiled for 8 hours and then evaporated to dryness under reduced pressure. The residue was dissolved in 1 liter of water and washed with two 500-ml portions of diethyl ether. The aqueous layer was adjusted to pH 3 with hydrochloric acid and extracted with 500 ml of chloroform. The chloroform layer was washed with water and evaporated to dryness under reduced pressure. The residue was dissolved in 100 ml of acetone and the solution was allowed to cool to give 20 g of 1-(4-benzyloxy-3-methylbenzyl)-4-chloro-2-phenylimidazole-5-acetic acid as colorless needles, which were washed with diethyl ether and recovered by filtration, m.p. 177°-178° C.

Elemental analysis: Calcd. for $C_{26}H_{23}N_2O_3Cl$: C, 69.87; H, 5.18; N, 6.26; Found: C, 69.61; H, 5.32; N, 6.01;

Reference Example 2

1-(4-Benzyloxy-3-methylbenzyl)-4-chloro-5-cyanomethylimidazole (10 g) was boiled in 100 ml of trifluoroacetic acid for 15 minutes. The reaction mixture was then evaporated to dryness and the residue was chromatographed on a column of silica gel (100 g) using chloroform as an eluent. The desired fractions were combined and concentrated to about 20 ml to give 3.7 g of 4-chloro-5-cyanomethyl-1-(4-hydroxy-3-methylbenzyl)-2-phenylimidazole as colorless prisms, m.p. 194°-196° C.

Elemental analysis: Calcd. for $C_{19}H_{16}N_3OCl$: C, 67.55; H, 4.78; N, 12.42; Found: C, 67.10; H, 4.78; N, 12.10;

the compound (VII) is generally used in a proportion of 1 to 5 molar equivalents.

Just as in the case of compound (I), the product compound (VI) can be easily isolated by the conventional separation procedure and can also be obtained as a salt with a physiologically acceptable acid or base.

The compound (VI) and salt thereof, like the compound (I), are of low toxicity, have desirable diuretic actions and antagonize the vasoconstrictive and hypertensive actions of angiotensin II so that they are of value for the treatment of edema and hypertension of various etiologies. The administration regimens and other conditions of use for the compound (VI) may be similar to those mentioned for the compound (I).

BEST MODE FOR CARRYING OUT THE INVENTION

Example 1

4-Chloro-1-(4-methoxy-3-methylbenzyl)-2-phenylimidazole-5-acetic acid (2 g) was suspended in 150 ml of acetonitrile, and 4 ml of trimethylsilyl iodide was added. The mixture was stirred in an argon stream at 90° C. for 48 hours. The reaction mixture was concentrated to dryness and the residue was shaken with 100 ml each of chloroform and water. The chloroform layer was washed with water and dried under reduced pressure. The residue was purified by column chromatography using 100 g of silica gel and recrystallization from acetone-diethyl ether to give 1.1 g of 4-chloro-1-(4-hydroxy-3-methylbenzyl)-2-phenylimidazole-5-acetic acid as colorless needles, m.p. 193°–195° C. (decompn.).

Elemental analysis: Calcd. for $C_{19}H_{17}N_2O_3Cl$: C, 63.96; H, 4.80; N, 7.85; Found: C, 64.06; H, 4.86; N, 7.88;

Example 2

4-Chloro-1-(4-benzyloxy-3-methylbenzyl)-2-phenylimidazole-5-acetic acid (20 g) was boiled in 200 ml of trifluoroacetic acid for 30 minutes. The reaction mixture was evaporated to dryness under reduced pressure and the residue was dissolved in 300 ml of diethyl ether and washed with two 300-ml portions of water. The diethyl ether layer was extracted with six 150-ml portions of 0.3 N-sodium hydroxide. The aqueous layers containing the desired product were combined, adjusted to pH 2 with hydrochloric acid and extracted with four 200-ml portions of ethyl acetate. The ethyl acetate layer was evaporated to dryness under reduced pressure and the residue was dissolved in 20 ml of acetone, followed by addition of 30 ml of diethyl ether to give 10 g or 4-chloro-1-(4-hydroxy-3-methylbenzyl)-2-phenylimidazole-5-acetic acid as colorless needles, m.p. 193°–195° C. (decompn.).

The IR spectrum (KBr) of this product was in good agreement with that of the compound obtained in Example 1.

Example 3

4-Chloro-1-(4-methoxy-3-methylbenzyl)-2-phenylimidazole-5-acetic acid (2.2 g) was stirred in 20 ml of 57% hydrobromic acid at 100°–110° C. for 2 hours. To the reaction mixture was then added 80 ml of water and the mixture was allowed to stand. The resulting syrupy precipitate was dissolved in 50 ml of ethyl acetate and washed with water. The ethyl acetate layer was evaporated to dryness and the residue was purified by column chromatography using 50 g of silica gel. The desired fractions were combined and crystallized from acetone-diethyl ether to give 0.3 g of 4-chloro-1-(4-hydroxy-3-methylbenzyl)-2-phenylimidazole-5-acetic acid as colorless needles, m.p. 190°–193° C. (decompn.).

The IR spectrum (KBr) of this product was in good agreement with that of the compound obtained in Example 1.

Example 4

4-Chloro-5-cyanomethyl-1-(4-hydroxy-3-methylbenzyl)-2-phenylimidazole (1 g) was dissolved in 10 ml of ethanol, and 10 ml of 2 N-sodium hydroxide was added. The mixture was boiled for 4 hours and evaporated to dryness, and the residue was shaken with 20 ml each of chloroform and water. The aqueous layer was washed with chloroform and 10 ml of 2N-hydrochloric acid was added. The resulting syrupy precipitate was recrystallized from aqueous ethanol to give 0.5 g of 4-chloro-1-(4-hydroxy-3-methylbenzyl)-2-phenylimidazole-5-acetic acid as colorless needles, m.p. 192°–195° C. (decompn.).

Example 5

4-Chloro-1-(4-hydroxy-3-methylbenzyl)-2-phenylimidazole-5-acetic acid (3.6 g) was dissolved in 20 ml of ethanol, and 5 ml of 2N-sodium hydroxide and then 200 ml of acetone were added to give 3 g of the sodium salt of the above compound as colorless scales, m.p. 195°–200° C. (decompn.).

Elemental analysis Calcd. for $C_{19}H_{16}N_2O_3ClNa$: C, 60.25; H, 4.26; N, 7.39; Found: C, 60.18; H, 4.34; N, 7.52;

Example 6

4-Chloro-1-(4-ethoxy-3-methylbenzyl)-2-phenylimidazole-5-acetic acid (10 g) was stirred in 90 ml of 57% hydrobromic acid at 80°–90° C. for 6 hours. The reaction mixture was evaporated to dryness under reduced pressure and the residue was dissolved in 200 ml of ethyl acetate and washed three times with water. The ethyl acetate layer was evaporated to dryness under reduced pressure and the residue was purified by column chromatography using 210 g of silica gel. The desired fractions were recrystallized from acetone-diethyl ether to give 3 g of 4-chloro-1-(4-hydroxy-3-methylbenzyl)-2-phenylimidazole-5-acetic acid as colorless needles, m.p. 190°–192° C. (decompn.).

Example 7

4-Chloro-1-(4-methoxy-3-methylbenzyl)-2-phenylimidazole-5-acetic acid (1.1 g) was suspended in 20 ml of dichloromethane and 4 ml of a dichloromethane solution containing 1 g of boron tribromide was added dropwise under stirring at room temperature. A precipitate separated out immediately after dissolution of the starting material. The mixture was allowed to stand for 6 hours. The supernatant was discarded and the precipitate was stirred with 50 ml each of ethyl acetate and water. The ethyl acetate layer was washed with water and evaporated to dryness under reduced pressure. The residue was washed with a small amount of acetone and recrystallized from aqueous alcohl to give 0.8 g of 4-chloro-1-(4-hydroxy-3-methylbenzyl)-2-phenylimidazole-5-acetic acid as colorless scales, m.p. 193°–195° C. (decompn.).

Elemental analysis: Calcd. for $C_{19}H_{17}N_2O_3Cl$: C, 63.96; H, 4.80; N, 7.85; Found: C, 64.03; H, 4.80; N, 7.93;

Reference Example 3

4-Chloro-1-(4-hydroxy-3-methylbenzyl)-2-phenylimidazole-5-acetic acid (1.1 g) was dissolved in 10 ml of pyridine, then 2 ml of acetic anhydride was added, and the mixture was stirred at room temperature for 2 hours and evaporated to dryness under reduced pressure. The residue was purified by column chromatography using 20 g of silica gel. The desired fractions were combined and evaporated to dryness under reduced pressure and the residue was recrystallized from aqueous ethanol to give 0.7 g of 4-chloro-1-(4-acetoxy-3-methylbenzyl)-2-phenylimidazole-5-acetic acid as colorless needles, m.p. 200°–203° C.

Elemental analysis: Calcd. for $C_{21}H_{19}N_2O_4Cl.1/2\text{-}H_2O$: C, 61.84; H, 4.94; N, 6.87; Found: C, 62.06; H, 4.69; N, 6.95;

Reference Example 4

4-Chloro-1-(4-hydroxy-3-methylbenzyl)-2-phenylimidazol-5-acetic acid (0.8 g) was dissolved in 10 ml of pyridine, 2 ml of butyric anhydride was added, and the mixture was stirred at room temperature for 15 hours and then evaporated to dryness under reduced pressure. The residue was purified by column chromatography using 30 g of silica gel. The desired fractions were combined and evaporated to dryness under reduced pressure and the residue was recrystallized from aqueous ethanol to give 0.75 g of 4-chloro-1-(4-n-butyryloxy-3-methylbenzyl)-2-phenylimidazole-5-acetic acid as colorless prisms, m.p. 165°–170° C.

Elemental analysis: Calcd. for $C_{23}H_{23}N_2O_4Cl$: C, 64.71; H, 5.43; N, 6.56; Found: C, 65.01; H, 5.31; N, 6.65;

Experimental Example 1

Angiotensin II (briefly, AII)-antagonizing activity of the compound (I) of this invention (rabbit aortic vessel)

The method of preparing the aortic vessel specimens and the reaction conditions employed were as described in European Journal of Pharmacology 18, 316 (1972). AII was used in a concentration of $4 \times 10^{-9}$ M, and the change in isometric tension of the untreated vessel specimen was measured as control. As a test, the vessel was treated with the test compound for 15 minutes and a similar determination was made. The two results were compared and the inhibition rate was calculated by means of the following formula.

Inhibition rate (%)

Inhibition rate (%) =

$$\frac{\text{(Change (g) in isometric tension of untreated vessel by AII } - \text{ change (g) in isometric tension of treated vessel by AII)}}{\text{Change (g) in isometric tension of untreated vessel by AII}} \times 100$$

The results are shown in Table 1.

TABLE 1

| Compound (Example No.) | Concentration of drug (M) | Inhibition rate (%) |
| --- | --- | --- |
| Example 1 | $10^{-5}$ | 100 |
|  | $10^{-6}$ | 75 |
| 4-Chloro-1-(4-hydroxybenzyl)-2-phenylimidazole-5-acetic acid (known compound) | $10^{-5}$ | 46 |

Experimental Example 2

The diuretic action of the compound (I) of this invention is shown in Table 2. The test was conducted in rats and dogs, in accordance with the method of W. L. Lipschitz. The numerals in the table denote the values for the treated groups with the value for control group being taken as 1.00.

$$UV = \frac{\text{Urine volume of animals in treated group (ml/6 hrs./100 g body weight)}}{\text{Urine volume of animals in control group (ml/6 hrs./100 g body weight)}}$$

$$U_{Na}V = \frac{\text{Excretion of sodium by animals in treated group (}\mu\text{ equiv./6 hrs./100 g body weight)}}{\text{Excretion of sodium by animals in control group (}\mu\text{ equiv./6 hrs./100 g body weight)}}$$

$$U_KV = \frac{\text{Excretion of potassium by animals in treated group (}\mu\text{ equiv./6 hrs./100 g body weight)}}{\text{Excretion of potassium by animals in control group (}\mu\text{ equiv./6 hrs./100 g body weight)}}$$

TABLE 2

| Compound (Example No. or Ref. Example No.) | Animal species | Dosage (mg/kg, P.O.) | Diuretic action | | |
| --- | --- | --- | --- | --- | --- |
| | | | UV | $U_{Na}V$ | $U_KV$ |
| Ref. Example 3 | Rat (n = 6) | 30 | 8.22*** | 6.54*** | 2.92** |
| Ref. Example 4 | Rat (n = 6) | 30 | 6.69*** | 5.82*** | 2.80** |
| 4-Chloro-1-(4-methoxy-3-methylbenzyl)-2-phenylimidazole-5-acetic acid (known compound) | Rat (n = 6) | 30 | 8.25*** | 6.36*** | 3.33** |
| Example 1 | Dog (n = 3) | 3 | 3.41** | 2.97** | 2.20** |
| | | 30 | 5.11** | 4.24** | 4.88** |
| 4-Chloro-1-(4-methoxy-3-methylbenzyl)-2-phenylimidazole-5-acetic acid (known compound) | Dog (n = 3) | 3 | 1.20 | 1.10 | 0.86 |
| | | 30 | 1.67 | 1.73* | 2.53* |

*$P < 0.05$,
**$P < 0.01$,
***$P < 0.001$

Experimental Example 3

Antihypertensive action in dogs with renal hypertension

Male adult beagle dogs were laparotomized under pentobarbital anesthesia and the left renal artery was constricted with a silver clip so as to reduce the renal blood flow to about 30%. After the operation, the animals were kept for at least 2 months and the individuals having a systolic pressure of at least about 180 mmHg were used in the test. The blood levels of renin were normal during the time indicating that the dogs were in the chronic phase of renal hypertension. Blood pressure determinations were made using a plethysmograph (Narco, DE-300). Each drug was sealed in a gelatin capsule and administered by the oral route. The blood pressure was monitored up to 8 hours after administration. The results are shown in Table 3.

TABLE 3

| Compound (Example No.) | Dose (mg) | | Before administration | After 1 hr. | After 2 hrs. | After 4 hrs. | After 8 hrs. |
|---|---|---|---|---|---|---|---|
| | | | Blood pressure (mmHg) | | | | |
| Example 1 | 10 | Systolic | 201 ± 5 | 189 ± 5 | 165 ± 6* | 155 ± 8* | 167 ± 8 |
| (n = 3) | | Diastolic | 124 ± 2 | 123 ± 4 | 93 ± 7* | 89 ± 7* | 110 ± 8 |
| 4-Chloro-1-(4-methoxy-3-methylbenzyl)-2-phenyl-imidazole-5-acetic acid (n = 4) | 10 | Systolic | 189 ± 2 | 185 ± 5 | 181 ± 6 | 181 ± 2 | 188 ± 5 |
| | | Diastolic | 123 ± 6 | 113 ± 6 | 116 ± 7 | 115 ± 4 | 115 ± 5 |

*$P < 0.05$

Industrial Applicability

4-Chloro-2-phenylinidazole-5-acetic acid imidazole derivatives (I) provided by this invention have excellent pharmacological actions and are of use as drugs.

We claim:

1. A compound of the formula

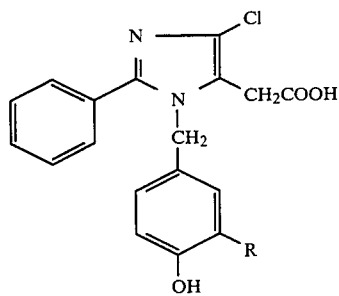

wherein R is lower alkyl, or a salt thereof.

2. A compound according to claim 1, wherein R is methyl.

3. A compound according to claim 1, wherein the salt is an alkaline metal salt.

4. A compound according to claim 1, which is 4-chloro-1-(4-hydroxy-3-methylbenzyl)-2-phenylimidazole-5-acetic acid.

5. A pharmaceutical composition which contains an effective amount for producing diuretic activity in a mammal of a compound of claim 1 and a carrier, vehicle or diluent therefor.

6. A pharmaceutical composition which contains an effective amount for producing hypotensive activity in a mammal of a compound of claim 2 and a carrier, vehicle or diluent therefor.

7. A method for producing hypotensive activity in a mammal, which comprises administering to said mammal an effective amount of a compound of claim 1.

8. A method for producing hypotensive activity in a mammal, which comprises administering to said mammal an effective amount of a compound of claim 2.

9. A method for producing hypotensive activity in a mammal, which comprises administering to said mammal an effective amount of a compound of claim 3.

10. A method for producing hypotensive activity in a mammal, which comprises administering to said mammal an effective amount of a compound of claim 4.

11. A method for producing diuretic activity in a mammal, which comprises administering to said mammal an effective amount of a compound of claim 1.

12. A method for producing diuretic activity in a mammal, which comprises administering to said mammal an effective amount of a compound of claim 2.

13. A method for producing diuretic activity in a mammal, which comprises administering to said mammal an effective amount of a compound of claim 3.

14. A method for producing diuretic activity in a mammal, which comprises administering to said mammal an effective amount of the compound of claim 4.

* * * * *